(12) United States Patent
Amberg et al.

(10) Patent No.: US 7,368,528 B2
(45) Date of Patent: May 6, 2008

(54) ANTINEOPLASTIC PEPTIDES

(75) Inventors: Wilhelm Amberg, Friedrichsdorf (DE); Teresa Barlozzari, Wellesley, MA (US); Harald Bernard, Bad Durkheim (DE); Ernst Buschmann, Ludwigshafen (DE); Andreas Haupt, Westborough, MA (US); Hans-Guenther Hege, Neustadt (DE); Bernd Janssen, Marlborough, MA (US); Andreas Kling, Manneim (DE); Helmut Lietz, Neustadt (DE); Kurt Ritter, Heidelberg (DE); Martina Ullrich, Schrieshaim (DE); Jurgen Weyman, Bad Durkheim (DE); Thomas Zierke, Bohl-Iggelheim (DE)

(73) Assignee: Abbott GmbH & Co. KG (DE)

( * ) Notice: Subject to any disclaimer, the term of this patent is extended or adjusted under 35 U.S.C. 154(b) by 0 days.

(21) Appl. No.: 11/179,074

(22) Filed: Jul. 11, 2005

(65) Prior Publication Data

US 2006/0009392 A1  Jan. 12, 2006

Related U.S. Application Data

(60) Division of application No. 09/757,142, filed on Jan. 9, 2001, now abandoned, which is a continuation of application No. 09/097,184, filed on Jun. 12, 1998, now abandoned, which is a continuation-in-part of application No. PCT/EP96/05518, filed on Dec. 11, 1996.

(60) Provisional application No. 60/059,062, filed on Dec. 15, 1995.

(51) Int. Cl.
  *C07K 7/00* (2006.01)
  *A61K 38/00* (2006.01)
(52) U.S. Cl. .................... 530/323; 530/330
(58) Field of Classification Search ............... 530/323, 530/330
  See application file for complete search history.

(56) References Cited

U.S. PATENT DOCUMENTS

| | | | |
|---|---|---|---|
| 4,816,444 A | 3/1989 | Pettit et al. | |
| 5,502,032 A | 3/1996 | Haupt et al. | |
| 5,504,191 A | 4/1996 | Pettit et al. | |
| 5,530,097 A | 6/1996 | Pettit et al. | |
| 5,554,725 A | 9/1996 | Pettit | |
| 5,831,002 A * | 11/1998 | Haupt et al. | 530/329 |
| 5,864,012 A | 1/1999 | Amberg et al. | |
| 5,886,147 A | 3/1999 | Amberg et al. | |
| 5,965,700 A | 10/1999 | Amberg et al. | |
| 6,015,790 A | 1/2000 | Barlozzari et al. | |
| 6,103,698 A | 8/2000 | Barlozzari et al. | |
| 6,143,721 A | 11/2000 | Janssen et al. | |
| 6,248,865 B1 | 6/2001 | Amberg et al. | |
| 6,458,765 B1 | 10/2002 | Janssen et al. | |
| 6,632,795 B1 | 10/2003 | Barlozzari et al. | |
| 2003/0153505 A1 | 8/2003 | Janssen et al. | |

FOREIGN PATENT DOCUMENTS

| DE | 4415997 A1 | 11/1995 |
|---|---|---|
| EP | 0398558 B1 | 11/1990 |
| EP | 0598129 B1 | 5/1994 |
| WO | WO-92/02541 A1 | 2/1992 |
| WO | WO-93/23424 A1 | 11/1993 |
| WO | WO-95/30690 A1 | 11/1995 |
| WO | WO-95/30691 A1 | 11/1995 |
| WO | WO-96/40751 A1 | 12/1996 |
| WO | WO-96/40752 A1 | 12/1996 |
| WO | WO-97/17364 A1 | 5/1997 |

OTHER PUBLICATIONS

Tasidotin HCI Genzyme, 2005, Current Opinion in Investigational Drugs, 6(6): 631-638.*
Pettit, G.R., et al., "The Isolation and Structure of a Remarkable Marine Animal Antineoplastic Constituent: Dolastatin 10," *J. Am. Chem. Soc.*, vol. 109:6883-6885 (1987).
Bai, R., et al., "Structure-Activity Studies with Chiral Isomers and with Segments of teh Antimitotic Marine Peptide Dolastatin 10," *Biochemical Pharmacology*, vol. 40(8):1859-1864 (1990).
Pettit, G.R., et al., "Antineoplastic Agents. 220. Synthesis of Natural (-)—Dolastatin 15," *J. Chem. Soc.*, vol. 113:6692-6693 (1991).
Bai, R., et al., "Dolastatin 15, a potent antimitotic depsipeptide derived from Dolabella auricularia. Interaction with tubulin and effects on cellular microtubules," *Biochemical Pharmacology*, vol. 43: 2637-2645 (1992).
Pettit, G.R., et al., "Isolation and Structure of the Cytostatic Depsipeptide Dolastatin 13 from the Sea Hare Dolabella auricularia," *J. Am. Chem. Soc.*, vol. 111(13):5015-5017 (1989).
Pettit, G.R., et al., "Antineoplastic Agents 337. Synthesis of Dolastatin-10 Structural Modifications," *Anti-Cancer Drug Design*, vol. 10:529-544 (1995).
Miyazaki, K., et al., "Synthesis and Antihumor Activity of Novel Dolastatin-10 Analogs," *Chem. Pharm. Bull.*, vol. 43(10):1706-1718 (1995).
Pettit, G.R., et al., "Isolation and Structure of the Cytostatic Linear Depsipeptide Dolastatin 15," *J. Org. Chem.* vol. 54:6005-6006 (1989).
Pettit, G.R., et al., "The Dolastatins 20. A convenient synthetic route to Dolastatin 15," *Tetrahedron*, vol. 50(42):12097-12108 (1994).
Pettit, G.R., et al., "Isolation of Dolastatin 10-15 from the Marine Mollusc Dolabella Auricularia," *Tetrahedron*, vol. 49(42):9151-9170 (1993).

* cited by examiner

*Primary Examiner*—Jon D. Epperson
*Assistant Examiner*—Amber D. Steele
(74) *Attorney, Agent, or Firm*—Lahive & Cockfield LLP; Giulio A. DeConti, Jr.; Brian C. Trinque

(57) ABSTRACT

The present invention provides antineoplastic peptides of formula I,

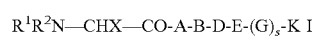

$R^1R^2N$—CHX—CO-A-B-D-E-$(G)_s$-K  I wherein $R^1$, $R^2$, X, A, B, D, E, G, K, and s have the meanings stated in the description. The compounds have antineoplastic activity.

2 Claims, No Drawings

ANTINEOPLASTIC PEPTIDES

RELATED APPLICATIONS

This application is a divisional of U.S. patent application Ser. No. 09/757,142, filed Jan. 9, 2001, now abandoned which is a continuation of U.S. patent application Ser. No. 09/097,184, filed Jun. 12, 1998, now abandoned which is a continuation-in-part of International Application Serial No. PCT/EP96/05518, filed Dec. 11, 1996, which designated the United States, published in English, which claims priority to U.S. Provisional Patent Application Ser. No. 60/059,062, entitled "Antineoplastic Peptides", which resulted from the conversion of U.S. patent application Ser. No. 08/573,422, filed Dec. 15, 1995, now abandoned.

The entire teachings of the above application(s) are incorporated herein by reference.

FIELD OF THE INVENTION

The invention described herein provides novel peptides and derivatives thereof which offer potentially improved therapeutic utilities for the treatment of neoplastic diseases as compared to dolastatin −10 and −15 (U.S. Pat. Nos. 4,879,276 and 4,816,444) and the compounds described in WO 93/23424.

SUMMARY OF THE INVENTION

Compounds of this invention include novel peptides of the formula I $$R^1R^2N\text{—}CHX\text{—}CO\text{-}A\text{-}B\text{-}D\text{-}E\text{-}(G)_s\text{-}K \qquad I$$

where
$R^1$ is hydrogen, methyl, or ethyl;
$R^2$ is methyl; or ethyl; or
$R^1$—N—$R^2$ together are a pyrrolidine ring;
A is a valyl, isoleucyl, allo-isoleucyl, 2-tert-butylglycyl, 2-ethylglycyl, norleucyl or norvalyl residue;
B is a N-methyl-valyl, N-methyl-norvalyl, N-methyl-leucyl, N-methyl-isoleucyl, N-methyl-2-tert-butylglycyl, N-methyl-2-ethylglycyl, or N-methyl-norleucyl residue;
D is a prolyl, homoprolyl, hydroxyprolyl, or thiazolidine-4-carbonyl residue;
E is a prolyl, homoprolyl, hydroxyprolyl, thiazolidine-4-carbonyl, trans-4-fluoro-L-prolyl, cis-4-fluoro-L-prolyl, trans-4-chloro-L-prolyl or cis-4-chloro-L-prolyl residue;
X is ethyl, propyl, butyl, isopropyl, sec. butyl, tert.-butyl, cyclopropyl, or cyclopentyl;
G is a L-2-tert.butylglycyl, D-2-terr.butylglycyl, D-valyl, D-isoleucyl, D-leucyl, D-norvalyl, 1-aminopentyl-1-carbonyl, or 2,2-dimethylglycyl residue;
s is 0 or 1;
K is —NH—$C_{1-8}$-alkyl, —NH—$C_{3-8}$-alkenyl, —NH—$C_{3-8}$-alkinyl, —NH—$C_{6-8}$-cycloalkyl, —NH—$C_{1-4}$-alkene-$C_{3-8}$-cycloalayl, $C_{1-4}$-alkyl-N—$C_{1-6}$-alkyl, in which residues one $CH_2$ group may be replaced by O or S, one H by phenyl or cyano, or 1, 2 or 3 H by F, except the N-methoxy-N-methylamino, N-benzylamino, or N-methyl-N-benzylamino residue, or K is and the salts thereof with physiologically tolerated acids.

DETAILED DESCRIPTION OF THE INVENTION

In specific embodiments of the compounds of formula I, K may be —$NHCH_3$, —$NHCH_2CH_3$, —$NH(CH_2)_2CH_3$, —$NH(CH_2)_3CH_3$, —$NH(CH_2)_4CH_3$, —$NH(CH_2)_5CH_3$, —$NH(CH_2)_6CH_3$, —$NHCH(CH_2)_7CH_3$, —$NHCH(CH_3)_2$, —$NHCH(CH_3)CH_2CH_3$, —$NHCH(CH_2CH_3)_2$, —$NHCH(CH_2CH_2CH_3)_2$, —$NHC(CH_3)_3$, —$NHCH(CH_2CH_3)CH_2CH_3$, —$NHCH(CH_3)CH(CH_3)_2$, —$NHCH(CH_2CH_3)CH(CH_3)_2$, —$NHCH(CH_3)C(CH_3)_3$, —NH-cyclohexyl, —NH-cycloheptyl, —NH-cyclooctyl, —$N(CH_3)OCH_2CH_3$, —$N(CH_3)OCH_2CH_2CH_3$, —$N(CH_3)OCH(CH_3)_2$, —$N(CH_3)O(CH_2)_3CH_3$, —$N(CH_3)OCH_2C_6H_5$, —NH —(CH₂)₂C₆H₅, —NH(CH₂)₃C₆H₅, —NHCH(CH₃)C₆H₅, —NHC(CH₃)₂C₆H₅, —NHC(CH₃)₂CH₂CH₃, —NHC(CH₃)(CH₂CH₃)₂, —NHCH[CH(CH₃)₂]₂, —NHC(CH₃)₂CN, —NHCH(CH₃)CH(OH)C₆H₅, —NHCH₂-cyclohexyl, —NHCH₂C(CH₃)₃, —NHCH₂CH(CH₃)₂, —N(CH₃)₂, —N(CH₂CH₃)₂, —N(CH₂CH₂CH₃)₂, —NHCH₂CF₃, —NHCH(CH₂F)₂, —NHCH₂CH₂F, —NHCH₂CH₂OCH₃, —NHCH₂CH₂SCH₃, —NHCH₂CHCH₂, —NH—C(CH₃)₂CH═CH₂, —NHC(CH₃)₂C≡CH, —NHC(CH₂CH₃)₂C≡CH, —NHC(CH₃)₂CH₂CH₂OH, —NH(CH₂CH₂O)₂CH₂CH₃, —NHC(CH₃)₂CH(CH₃)₂, —NHC(CH₃)₂CH₂CH₂CH₃, —NHC(CH₃)₂CH₂C₆H₅, —N(OCH₃)CH(CH₃)₂, —N(OCH₃)CH₂CH₃, —N(OCH₃)CH₂CH₂CH₃, —N(OCH₃)CH₂C₆H₅, —N(OCH₃)C₆H₅, —N(CH₃)OC₆H₅, —NHCH[CH(CH₃)₂]₂, —N(OCH₃)CH²CH₂CH₂CH₃, or the special ring systems mentioned above.

In one embodiment of the compounds of formula I described above, s is 0 and E is homoprolyl or hydroxyprolyl.

Preferred are compounds of the formula I where the substituents R¹, R², A, B, D, E, X, G and s have the following meanings:

R¹ hydrogen, methyl, or ethyl, especially methyl;

R² methyl or ethyl, especially methyl;

A valyl, isoleucyl, 2-tert-butylglycyl, 2-ethylglycyl, norleucyl or norvalyl, especially valyl, isoleucyl, 2-tert-butylglycyl, 2-ethylglycyl, B N-methyl-valyl, N-methyl-norvalyl, N-methyl-isoleucyl, N-methyl-2-tert-butylglycyl, N-methyl-2-ethylglycyl, or N-methyl-norleucyl, especially N-methyl-valyl, N-methyl-2-ethylglycyl, N-methyl-norleucyl, N-methyl-isoleucyl, or N-methyl-2-tert.butyl-glycyl;

D prolyl, homoprolyl or thiazolidine-4-carbonyl, especially prolyl or thiazolidine-4-carbonyl;

E prolyl, homoprolyl, thiazolidine-4-carbonyl, trans-4-fluoro-L-prolyl, cis-4-fluoro-L-prolyl, trans-4-chloro-L-prolyl or cis-4-chloro-L-prolyl, especially prolyl, trans-4-fluoro-prolyl, cis-4-fluoro-prolyl, trans-4-chloro-prolyl, or cis-4-chloro-prolyl;

X ethyl, propyl, isopropyl, sec.butyl, tert.butyl or cyclopropyl, especially ethyl, isopropyl, sec.butyl or tert.butyl;

G L-2-tert.butylglycyl, D-2-tert.butylglycyl, D-valyl, D-isoleucyl, D-leucyl or 2,2-dimethylglycyl residue;

s 0 or 1.

Preferred meanings for K are:

—NH—C₁₋₈-alkyl, —NH—C₆₋₈-cycloalkyl, —NH—CH₂-cyclohexyl, C₁₋₄-alkyl-N—C₁₋₆-alkyl, in which residues one CH₂ group may be replaced by O, one H by phenyl or 1 or 2 H by F, except the N-methoxy-N-methylamino, N-benzylamino, or N-methyl-N-benzylamino residue, or K is

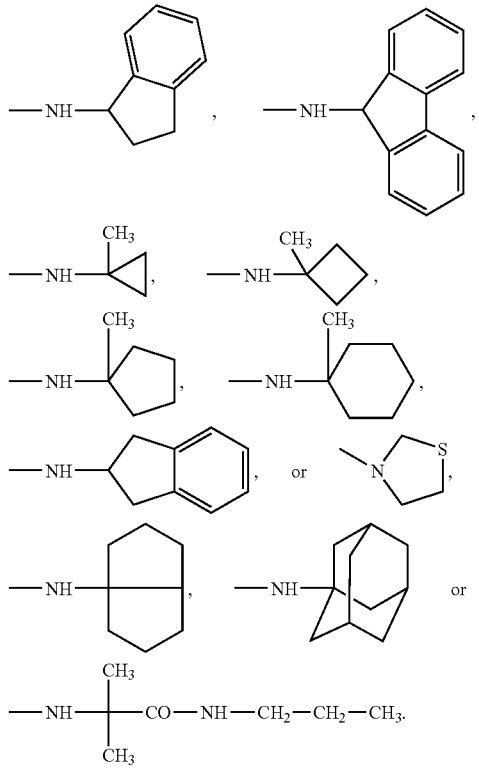

More preferred K is

—NHCH₃, —NHCH₂CH₃, —NH(CH₂)₂CH₃, —NH(CH₂)₃CH₃, —NH(CH₂)₄CH₃, —NH(CH₂)₅CH₃, —NH(CH₂)₆CH₃, —NH(CH₂)₇CH₃, —NHCH(CH₃)₂, —NHCH(CH₃)CH₂CH₃, —NHCH(CH₂CH₃)₂, —NHCH(CH₂CH₂CH₃)₂, —NHC(CH₃)₃, —NHCH(CH₂CH₃)CH₂CH₂CH₃, —NHCH(CH₃)CH(CH₃)₂, —NHCH(CH₂CH₃)CH(CH₃)₂, —NHCH(CH₃)C(CH₃)₃, —NH-cyclohexyl, —NH-cycloheptyl, —NH-cyclooctyl, —N(CH₃)OCH₂CH₃, —N(CH₃)OCH₂CH₂CH₃, —N(CH₃)OCH(CH₃)₂, —N(OCH₃)CH(CH₃)₂, —N(CH₃)OCH₂C₆H₅, —NH(CH₂)₂C₆H₅, —NH(CH₂)₃C₆H₅, —NHCH(CH₃)C₆H₅, —NHC(CH₃)₂C₆H₅, —NHC(CH₃)₂CH₂CH₃, —NHC(CH₃)(CH₂CH₃)₂, —NHCH(CH₃)CH(OH)C₆H₅, —NHCH₂-cyclohexyl, —N(CH₃)₂, —N(CH₂CH₃)₂, —N(CH₂CH₂CH₃)₂, —NHCH(CH₂F)₂, —NHC(CH₃)CH═CH₂, —NHC(CH₃)₂CN, —NHC(CH₃)₂C≡CH, —NHC(CH₃)₂CONH₂, —NHCH[CH(CH₃)₂]₂, —N(OCH₃)CH₂C₆H₅, —N(OCH₃)CH₂CH₃, —N(OCH₃)CH₂CH₂CH₃, —N(OCH₃)CH₂CH₂CH₂CH₃,

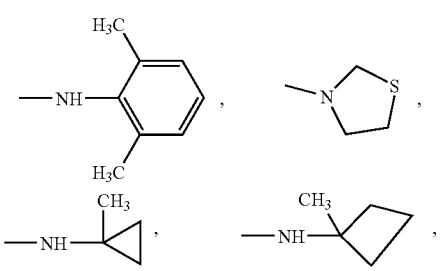

-continued

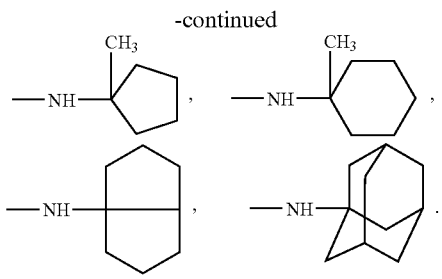

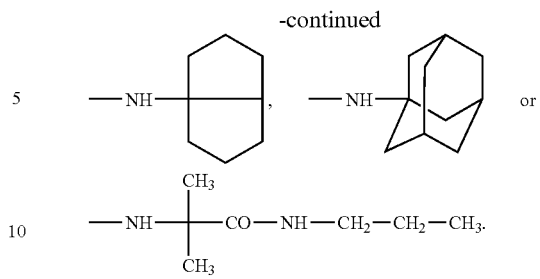

In one embodiment of the preferred compounds of formula I described above, s is 0 and E is homoprolyl or hydroxyprolyl.

Especially preferred are compounds of the formula I where $R^1$ and $R^2$ are methyl, A is a valyl, isoleucyl, 2-tert.-butylglycyl residue B is a N-methylvalyl, N-methyl-isoleucyl, N-methyl-2-tert.-butylglycyl residue, D is a prolyl or thiazolidine-4-carbonyl residue, E is a prolyl, cis-4-fluoro-L-prolyl, or cis-4-chloro-L-prolyl residue, X is a isopropyl, sec.-butyl, or tert.-butyl residue, s is 0, and K is
—NHCH(CH$_3$)$_2$, —NHCH(CH$_3$)CH$_2$CH$_3$, —NHCH(CH$_2$CH$_3$)$_2$, —NHCH(CH$_2$CH$_2$CH3)$_2$, —NHC(CH$_3$)$_3$, —NHCH(CH$_2$CH$_3$)CH$_2$CH$_2$CH$_3$, —NHCH(CH$_3$)CH(CH$_3$)$_2$, —NHCH(CH$_2$CH$_3$)CH(CH$_3$)$_2$, —NHCH(CH$_3$)C(CH$_3$)$_3$, —NH-cycloheptyl, —NH-cyclooctyl, —N(CH$_3$)OCH$_2$CH$_3$, —N(CH$_3$)OCH$_2$CH$_2$CH$_3$, —N(CH$_3$)OCH(CH$_3$)$_2$, —N(OCH$_3$)CH(CH$_3$)$_2$, —N(CH$_3$)OCH$_2$C$_6$H$_5$, —NH(CH$_2$)$_2$C$_6$H$_5$, —NH(CH$_2$)$_3$C$_6$H$_5$, —NHCH(CH$_3$)C$_6$H$_5$, —NHC(CH$_3$)$_2$C$_6$H$_5$, —NHC(CH$_3$)$_2$CH$_2$CH$_3$, —NHC(CH$_3$)(CH$_2$CH$_3$)$_2$, —NHCH(CH$_3$)CH(OH)C$_6$H$_5$, —NHCH(CH$_2$F)$_2$, —NHC(CH$_3$)$_2$CH$_2$CH$_2$OH, —NH(CH$_2$CH$_2$O)$_2$CH$_2$CH$_3$, —NHC(CH$_3$)$_2$CH═CH$_2$, —NHC(CH$_3$)$_2$CH(CH$_3$)$_2$, —N(OCH$_3$)CH$_2$CH$_3$, —N(OCH$_3$)CH$_2$CH$_2$CH$_3$, —N(OCH$_3$)CH$_2$CH$_2$CH$_2$CH$_3$, —NHC(Ch$_3$)$_2$CN, —NHC(CH$_3$)$_2$C≡CH, —NHCH[CH(CH$_3$)$_2$]$_2$, —NHC(CH$_3$)$_2$CONH$_2$, —NHC(CH$_3$)$_2$CH$_2$C$_6$H$_5$, —N(OCH$_3$)C$_6$H$_5$, —N(OCH$_3$)CH$_2$C$_6$H$_5$,

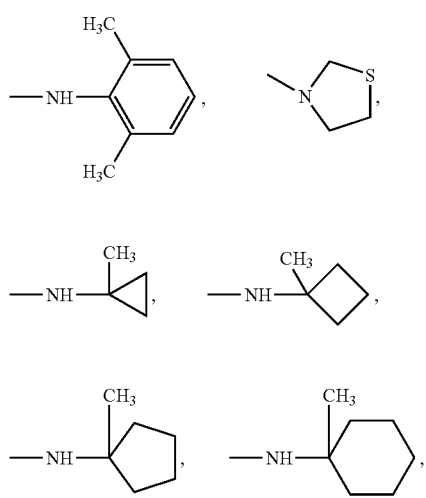

This invention also provides methods for preparing the compounds of formula I, pharmaceutical compositions containing such compounds together with a pharmaceutically acceptable carrier and methods for using same for treating cancer in mammals.

The new compounds may be present as salts with physiologically tolerated acids such as: hydrochloric acid, citric acid, tartaric acid, lactic acid, phosphoric acid, methanesulfonic acid, acetic acid, formic acid, maleic acid, fumaric acid, malic acid, succinic acid, malonic acid, sulfuric acid, L-glutamic acid, L-aspartic acid, pyruvic acid, mucic acid, benzoic acid, glucuronic acid, oxalic acid, ascorbic acid and acetylglycine.

The novel compounds can be prepared by known methods of peptide chemistry. Thus, the peptides can be assembled sequentially from amino acids or by linking suitable small peptide fragments. In the sequential assemblage, starting at the C terminus the peptide chain is extended stepwise by one amino acid each time. In fragment coupling it is possible to link together fragments of different lengths, and the fragments in turn can be obtained by sequential assemblage from amino acids or themselves by fragment-coupling.

Both in the sequential assemblage and in the fragment coupling it is necessary to link the units by forming an amide linkage. Enzymatic and chemical methods are suitable for this.

Chemical methods for forming the amide linkage are described in detail by Mueller, Methoden der organischen Chemie Vol. XV/2, pp 1 to 264, Thieme Verlag, Stuttgart, 1974; Stewart, Young, Solid Phase Peptide Synthesis, pp 31 to 34, 71 to 82, Pierce Chemical Company, Rockford, 1984; Bodanszky, Klausner, Ondetti, Peptide Synthesis, pp 85 to 128, John Wiley & Sons, New York, 1976; The Practice of Peptide Synthesis, M. Bodanszky, A. Bodanszky, Springer-Verlag, 1994, and other standard works on peptide chemistry. Particular preference is given to the azide method, the symmetric and mixed anhydride method, in situ generated or preformed active esters, the use of urethane protected N-carboxy anhydrides of amino acids and the formation of the amide linkage using coupling reagents, especially dicyclohexylcarbodiimide (DCC), diisopropylcarbodiimide (DIC), 1-ethoxycarbonyl-2-ethoxy-1,2-dihydroquinoline (EEDQ), pivaloylchloride, 1-ethyl-3-(3-dimethylaminopropyl)carbodiimide hydrochloride (EDCI), n-propanephosphonic anhydride (PPA), N,N-bis(2-oxo-3-oxazolodinyl)-amidophosphoryl chloride (BOP-Cl), bromo-tris-pyrrolidino-phosphonium hexafluorophosphate (PyBrop), diphenylphosphoryl azide (DPPA), Castro's reagent (BOP, PyBop), O-benzotriazolyl-N,N,N',N'-tetramethyluronium salts (HBTU), O-azabenzotriazolyl-N,N,N',N'-tetramethyluronium salts (HATU), diethylphosphoryl cyanide (DEPCN), 2,5-diphenyl-2,3-dihydro-3-oxo-4-hydroxythiophene dioxide (Steglich's reagent; HOTDO) and 1,1'-carbonyldiimidazole (CDI). The coupling reagents can be employed alone or in combination with additives such as N,N-dimethyl-4-aminopyridine (DMAP), N-hydroxy-benzotriazole (HOBt), N-hydroxybenzotriazine (HOOBt), Azabenzotriazole, N-hydroxysuccinimide (HOSu) or 2-hydroxypyridine.

Whereas it is normally possible to dispense with protective groups in enzymatic peptide synthesis, reversible protection of reactive groups not involved in formation of the amide linkage is necessary for both reactants in chemical synthesis. Three conventional protective group techniques are preferred for the chemical peptide synthesis: the benzyloxycarbonyl (Z), the t-butoxycarbonyl (Boc) and the 9-fluorenylmethoxycarbonyl (Fmoc) techniques.

Identified in each case is the protective group on the alpha-amino group of the chain-extending unit. A detailed review of amino-acid protective groups is given by Mueller, Methoden der organischem Chemie vol. XV/1, pp 20 to 906, Thieme Verlag, Stuttgart, 1974. The units employed for assembling the peptide chain can be reacted in solution, in suspension or by a method similar to that described by Merrifield in J. Amer. Chem. Soc. 85 (1963) 2149.

Suitable for peptide synthesis in solution are all solvents which are inert under the reaction conditions, especially water, N,N-dimethylformamide (DMF), dimethyl sulfoxide (DMSO), acetonitrile, dichloromethane (DCM), ethyl acetate, 1,4-dioxane, tetrahydrofuran (THF), N-methyl-2-pyrrolidone (NMP) and mixtures of the said solvents.

Peptide synthesis on the polymeric support can be carried out in all inert organic solvents in which the amino-acid derivatives used are soluble. However, preferred solvents additionally have resin-swelling properties, such as DMF, DCM, NMP, acetonitrile and DMSO, and mixtures of these solvents. After synthesis is complete, the peptide is cleaved off the polymeric support. The conditions under which cleavage off the various resin types is possible are disclosed in the literature. The cleavage reactions most commonly used are acid- and palladium-catalyzed, especially cleavage in liquid anhydrous hydrogen fluoride, in anhydrous trifluoromethanesulfonic acid, in dilute or concentrated trifluoroacetic acid, palladium-catalyzed cleavage in THF or THF-DCM mixtures in the presence of a weak base such as morpholine or cleavage in acetic acid/dichloromethane/trifluoroethanol mixtures. Depending on the chosen protective groups, these may be retained or likewise cleaved off under the cleavage conditions.

Partial deprotection of the peptide may also be worthwhile when certain derivatization reactions are to be carried out.

Peptides dialkylated at the N-terminus can be prepared either by coupling on the appropriate N,N-di-alkylamino acids in solution or on the polymeric support, by reductive alkylation of the resin-bound peptide in DMF/1% acetic acid with NaCNBH$_3$ and the appropriate aldehydes, by hydrogenation of the peptide in solution in the presence of aldehyde or ketone and Pd/C.

The various non-naturally occurring amino acids as well as the various non-amino acid moieties disclosed herein may be obtained from commercial sources or synthesized from commercially-available materials using methods known in the art. For example, amino acids building blocks with $R^1$ and $R^2$ moieties can be prepared according to E. Wuensch, Houben Weyl, Meth. d. Org. Chemie, Bd. XV, 1, p. 306 following, Thieme Verlag Stuttgart 1974 and Literature cited therein.

The compounds of this invention may be used to inhibit or otherwise treat solid tumors (e.g. tumors of the lung, breast, colon, prostate, bladder, rectum, or endometrial tumors) or hematological malignancies (e.g. leukemias, lymphomas) by administration of the compound to the mammal.

It is a special advantage of the new compounds that they are very resistant to enzymatic degradation and can also be administered orally.

Administration may be by any of the means which are conventional for pharmaceutical, preferably oncological, agents, including oral and parenteral means such as subcutaneously, intravenously, intramuscularly and intraperitoneally.

The compounds may be administered alone or in the form of pharmaceutical compositions containing a compound of formula I together with a pharmaceutically accepted carrier appropriate for the desired route of administration. Such pharmaceutical compositions may be combination products, i.e., may also contain other therapeutically active ingredients.

The dosage to be administered to the mammal will contain an effective tumor-inhibiting amount of active ingredient which will depend upon conventional factors including the biological activity of the particular compound employed; the means of administration; the age, health and body weight of the recipient; the nature of the the symptoms; the frequency of treatment; the administration of other therapies; and the effect desired. A typical daily dose will be about 0.05 to 50 milligrams body weight on oral administration and about 0.01 to 20 milligrams per kilogram of body weight on parenteral administration.

The novel compounds can be administered in conventional solid or liquid pharmaceutical administration forms, e.g. uncoated or (film-)coated tablets, capsules, powders, granules, suppositories or solutions. These are produced in a conventional manner. The active substances can for this purpose be processed with conventional pharmaceutical aids such as tablet binders, fillers preservatives, tablet disintegrants, flow regulators, plasticizers, wetting agents, dispersants, emulsifiers, solvents, sustained release compositions, antioxidants and/or propellant gases (cf. H. Sucker et al.: Pharmazeutische Technologie, Thieme-Verlag, Stuttgart, 1978). The administration forms obtained in this way normally contain 1-90% by weight of the active substance.

The following examples are intended to illustrate the invention. The proteinogenous amino acids are abbreviated in the examples using the known three-letter code. Other abbreviations used: Me$_2$Val=N,N-dimethylvaline, MeVal=N-methylvaline.

EXAMPLES

A. General Procedures

I. The peptides of the present invention are either synthesized by classical solution synthesis using standard Z- and Boc-methodology as described above or by standard methods of solid-phase synthesis using Boc and Fmoc protective group techniques.

In the case of solid phase synthesis, the N,N-dialkylpenta- or hexapeptide acids are liberated from the solid support and further coupled with the corresponding C-terminal amines in solution. BOP-Cl and PyBrop were used as reagents for coupling of the amino acid following the N-methylamino acids. The reaction times were correspondingly increased. For reductive alkylation of the N-terminus, the peptide-resin was deprotected at the N terminus and then reacted with a 3-fold molar excess of aldehyde or ketone in DMF/1% acetic acid with addition of 3 equivalents of NaCNBH$_3$.

After the reaction was complete (negative Kaisertest) the resin was washed several times with water, isopropanol, DMF and dichloromethane.

In solution synthesis, the use of either Boc-protected amino acid NCAs (N-tert.-butyloxycarbonyl-amino acid-N-carboxy-anhydrides), Z-protected amino acid NCAs (N-benzyloxycarbonyl-amino acid-N-carboxy-anhydrides), or the use of pivaloylchloride as condensing agent respectively is most advantageous for coupling of the amino acid following the N-methylamino acids. Reductive alkylation of the N terminus can e.g. be achieved by reaction of the N-terminally deprotected peptides or amino acids with the corresponding aldehydes or ketones using $NaCNBH_3$ or hydrogen, Pd/C.

II. Purification and Characterization of the Peptides

Purification was carried out by gel chromatography (SEPHADEX G-10, G-15/10% HOAc, SEPHADEX LH20/MeOH), medium pressure chromatography (stationary phase: HD-SIL C-18, 20-45 mikron, 100 Angstrom; mobile phase: gradient with A=0.1% TFA/MeOH, B=0.1% TFA/water), or preparative HPLC (stationary phase: Waters Delta-Pak C-18, 15 mikron, 100 Angstrom; mobile phase: gradient with A=0.1% TFA/MeOH, 3=0.1% TFA/water).

The purity of the resulting products was determined by analytical HPLC (stationary phase: 100 2.1 mm VYDAC C-18, 5 l, 300 A; mobile phase: acetonitrile-water gradient, buffered with 0.1% TFA, 40° C.).

Characterization was by amino-acid analysis and fast atom bombardment mass spectroscopy.

B. Specific Procedures

Example 1

(SEQ ID NO: 1)

$Me_2$Val-Val-MeVal-Pro-Pro-$NHCH(CH_3)_2$ a) Z-MeVal-Pro-OME 66.25 g (250 mmol) Z-MeVal-OH were dissolved in 250 ml dry dichloroniethane. After addition of 36.41 ml (262.5 mmol) triethylamine, the reaction mixture was cooled to −25° C. and 32.27 ml (262.5 mmol) pivaloyl chloride were added. After stirring for 2.5 h, 41.89 g (250 mmol) H-Pro-OMexChl in 250 ml dichloromethane, neutralized with 36.41 ml (262.5 mmol) triethylamine at 0° C., were added to the reaction mixture. Stirring continued for 2 h at −25° C. and overnight at room temperature. The reaction mixture was diluted with dichloromethane and thoroughly washed with saturated aqueous $NaHCO_3$ solution (3×), water (1×), 5% citric acid (3×) and saturated NaCl solution. The organic phase was dried over sodium sulfate and evaporated to dryness. The residue (91.24 g) was stirred with petroleum ether overnight and filtered. 62.3 g of product were obtained.

b) H—MeVal-Pro-OMe 48.9 g (130 mmol) Z-MeVal-Pro-OMe were dissolved in 490 ml methanol. After addition of 10.9 ml (130 mmol) concentrated hydrochloric acid and 2.32 g 10% Palladium/charcoal, the reaction mixture was hydrogenated. Filtration and evaporation to dryness yielded 36.32 g of the product.

c) Z-Val-MeVal-Pro-OMe 18.1 g (65 mmol) H—MeVal-Pro-OMe, 21.6 g (78 mmol) Z-Val-N-carboxyanhydride and 22.8 ml (130 mmol) diisopropylethylamine were stirred in 110 ml DMF at 40° C. for 2 d. After evaporation of DMF, dichloromethane was added and the organic phase washed with saturated aqueous $NaHCO_3$ solution (3×), water (1×), 4% citric acid (3×) and saturated NaCl solution. The organic phase was dried over sodium sulfate and evaporated to dryness. The product (29.3 g) was obtained as a viscous oil.

d) H-Val-MeVal-Pro-OMe 29.3 g (61.6 mmol) of Z-Val-MeVal-Pro-OMe were dissolved in 230 ml methanol. After addition of 1.15 g 10% Palladium/charcoal, the reaction mixture was hydrogenated. Filtration and evaporation to dryness yielded 21.96 g of the product.

e) Z-Val-Val-MeVal-Pro-OMe (SEQ ID NO: 2)

15.29 g (61 mmol) Z-Val-OH and 21.96 g (61 mmol) H-Val-MeVal-Pro-OMe were dissolved in 610 ml dichioromethane and cooled to 0° C. After addition of 8.16 ml (73.2 mmol) N-Methylmorpholine, 2.77 g (20.3 mmol) HOBt and 11.73 g (61 mmol) EDCI, the reaction mixture was stirred overnight at room temperature, diluted with dichloromethane and thoroughly washed with saturated aqueous $NaHCO_3$ solution (3×), water (1×), 5% citric acid (3×) and saturated NaCl solution. The organic phase was dried over sodium sulfate and evaporated to dryness to yield 31.96 g of the product.

f) Z-Val-Val-MeVal-Pro-OH (SEQ ID NO: 2)

31.96 g (57 mmol) Z-Val-Val-MeVal-Pro-OMe (SEQ ID NO: 2) were dissolved in 250 ml methanol. 102.6 ml of a 1 N LiOH solution was added and the mixture stirred overnight at room temperature. After addition of 500 ml water, the aqueous phase was washed three times with ethyl acetate, adjusted to pH 2 at 0° C. and extracted three times with ethyl acetate. The organic phase was dried over sodium sulfate and evaporated to dryness yielding 30.62 g of the desired product as a white solid.

g) Z-Val-Val-MeVal-Pro-Pro-$NHCH(CH_3)_2$ (SEQ ID NO: 1)

2 g (3.35 mmol) Z-Val-Val-MeVal-Pro-OH (SEQ ID NO: 2) and 0.664 g (3.35 mmol) H-Pro-$NHCH(CH_3)_2$ were dissolved in 34 ml of dry dichloromethane. After cooling to 0° C., 1.35 ml (12.1 mmol) N-methylmorpholine, 0.114 g (0.84 mmol) HOBt and 0.645 g (3.35 mmol) EDCI were added and the reaction mixture stirred overnight at room temperature. 80 ml dichloromethane were added and the organic phase thoroughly washed with saturated aqueous $NaHCO_3$solution (3×), water (1×), 5% citric acid (3×) and saturated NaCl solution (1×). The organic phase was dried over sodium sulfate and evaporated to dryness to yield 1.96 g of the product which was used in the next reaction without further purification.

h) $Me_2$Val-Val-MeVal-Pro-Pro-$NHCH(CH_3)_2$ (SEQ ID NO: 1)

1.96 g Z-Val-Val-MeVal-Pro-Pro-$NHCH(CH_3)_2$ (SEQ ID NO: 2) were dissolved in 11 ml methanol. 0.054 g 10% Pd/C were added under nitrogen atmosphere and the reaction mixture hydrogenated at room temperature for 4 h. After addition of 0.86 ml (11.24 mmol) of a 37% aqueous formaldehyde solution and 0.281 g 10% Pd/C, hydrogenation was continued for 5 h. Filtration and evaporation of the solvent gave rise to 2.77 g of crude product. Further purification was achieved by dissolving the peptide in water, adjusting the pH to 2 and extracting the aqueous phase three times with ethyl acetate. The aqueous phase was then adjusted to pH 8-9 and extracted four times with dichloromethane. The organic phase was dried over sodium sulfate to yield 1.37 g of purified product as a white foam. The compound was further purified using medium pressure liquid chromatography (10-50% A in 10 min.; 50-90% A in 320 min.). Fractions containing the product were combined, lyophilized, redissolved in water and the pH adjusted to 9 with 1 N LiOH. After extraction with dichloromethane, the organic phase was dried over sodium sulfate and evaporated to dryness. Lyophilization led to 500 mg of pure product, which was characterized by fast atom bombardment mass spectrometry ([M+H]$^+$=593).

Example 2

(SEQ ID NO: 1)

Me$_2$Val-Val-MeVal-Pro-Pro-NHC(CH$_3$)$_3$ i) Z-Val-Val-MeVal-Pro-Pro-NHC(CH$_3$)$_3$ (SEQ ID NO: 1)

2 g (3.35 mmol) Z-Val-Val-MeVal-Pro-OH (SEQ ID NO: 2) and 0.692 g (3.35 mmol) H-Pro-NHC(CH$_3$)$_3$ were dissolved in 34 ml of dry dichloromethane. After cooling to 0° C., 1.35 ml (12.1 mmol) N-methylmorpholine, 0.114 g (0.84 mmol) HOBt and 0.645 g (3.35 mmol) EDCI were added and the reaction mixture stirred overnight at room temperature. 80 ml dichloromethane were added and the organic phase thoroughly washed with saturated aqueous NaHCO$_3$ solution (3×), water (1×), 5% citric acid (3×) and saturated NaCl solution (1×). The organic phase was dried over sodium sulfate and evaporated to dryness to yield 1.8 g of the product which was used in the next reaction without further purification.

k) Me$_2$Val-Val-MeVal-Pro-Pro-NHC(CH$_3$)$_3$ (SEQ ID NO: 1)

1.8 g Z-Val-Val-MeVal-Pro-Pro-NHC(CH$_3$)$_3$ (SEQ ID NO: 1) were dissolved in 10 ml methanol. 0.049 g 10% Pd/C were added under nitrogen atmosphere and the reaction mixture hydrogenated at room temperature for 4 h. After addition of 0.86 ml (11.24 mmol) of a 37% aqueous formaldehyde solution and 0.252 g 10% Pd/C, hydrogenation was continued for 5 h. Filtration and evaporation of the solvent gave rise to 1.82 g of crude product. The compound was further purified using medium pressure liquid chromatography 910-50% A in 10 min.; 50-90% A in 320 min.). Fractions containing the product were combined, lyophilized, redissolved in water and the pH adjusted to 9 with 1 N LiOH. After extraction with dichloromethane, the organic phase was dried over sodium sulfate and evaporated to dryness. Lyophilization led to 547 mg of pure product, which was characterized by fast atom bombardment mass spectrometry ([M+H]$^+$=607).

The following compounds were prepared or can be prepared according to examples 1 and 2:

3. Xaa Val Xab Pro Xac
4. Xaa Val Xab Pro Xad
5. Xaa Val Xab Pro Xae
6. Xaa Val Xab Pro Xaf
7. Xaa Val Xab Pro Xag
8. Xaa Val Xab Pro Xah
9. Xaa Val Xab Pro Xai
10. Xaa Val Xab Pro Xak
11. Xaa Val Xab Pro Xal
12. Xaa Val Xab Pro Xam
13. Xaa Val Xab Pro Xan
14. Xaa Val Xab Pro Xao
15. Xaa Val Xab Pro Xap
10. Xaa Val Xab Pro Xaq
17. Xaa Val Xab Pro Xar
18. Xaa Val Xab Pro Xas
19. Xaa Val Xab Pro Xat
20. Xaa Val Xab Pro Xau
21. Xaa Val Xab Pro Xav
22. Xaa Val Xab Pro Xaw
23. Xaa Val Xab Pro Xax
24. Xdd Val Xab Pro Xay
25. Xaa Val Xab Pro Xaz
26. Xaa Val Xab Pro Xba
27. Xaa Val Xab Pro Xbb
28. Xaa Val Xbc Pro Xay
29. Xaa Val Xab Pro Xbd
30. Xaa Val Xab Pro Xbe
31. Xaa Val Xab Pro Xbf
32. Xaa Val Xab Pro Xbg
33. Xaa Val Xab Pro Xbh
34. Xaa Val Xab Pro Xbi
35. Xaa Val Xab Pro Xbk
36. Xaa Val Xab Pro Xbl
37. Xaa Val Xab Pro Xbm
38. Xaa Val Xab Pro Xbn
39. Xaa Val Xab Pro Xbo
40. Xaa Val Xab Pro Xbp
41. Xaa Val Xab Pro Xbq
42. Xaa Val Xab Pro Xbr
43. Xaa Val Xab Pro Xbs
44. Xaa Val Xab Pro Xbt
45. Xaa Val Xab Pro Xbu
46. Xaa Val Xab Pro Xbv
47. Xaa Val Xab Pro Xbw
48. Xaa Val Xab Pro Xbx
49. Xaa Val Xab Pro Xby
50. Xaa Val Xab Pro Xbz
51. Xaa Val Xab Pro Xca
52. Xaa Val Xab Pro Xcb
53. Xaa Val Xab Pro Xcc
54. Xaa Val Xab Pro Xcd
55. Xaa Val Xab Pro Xce
56. Xaa Val Xab Pro Xcf
57. Xaa Val Xab Pro Xay
58. Xaa Val Xab Pro Xch
59. Xaa Val Xab Pro Xci
60. Xaa Val Xab Pro Xck
61. Xaa Val Xab Pro Xcl
62. Xaa Val Xab Pro Xcm
63. Xaa Val Xab Pro Xcn
64. Xaa Val Xab Pro Xco
65. Xaa Val Xab Pro Xcp
66. Xaa Val Xab Pro Xcq
67. Xaa Val Xab Pro Xcr
68. Xaa Val Xab Pro Xcs
69. Xaa Val Xab Pro Xct
70. Xaa Val Xab Pro Xcu
71. Xcw Val Xab Pro Xcv
72. Xcx Val Xab Pro Xcv
73. Xaa Val Xab Pro Pro Xcy
74. Xaa Val Xab Pro Pro Xcz
75. Xaa Val Xda Pro Xcv
76. Xaa Xdb Xab Pro Xcv
77. Xdc Val Xab Pro Xcv
78. Xaa Ile Xab Pro Xcv
79. Xdd Val Xab Pro Xcv
80. Xde Val Xab Pro Xcv
81. Xaa Xdf Xab Pro Xcv
82. Xaa Val Xab Pro Xcg
83. Xaa Val Xab Pro Pro Xdg
84. Xaa Val Xab Pro Pro Xdh
85. Xaa Val Xab Pro Pro Xdi
86. Xaa Val Xab Pro Pro Xdk

87. Xaa Val Xdl Pro Xcv
88. Xde Val Xab Pro Xay
89. Xaa Val Xdl Pro Xay
90. Xaa Val Xab Pro Xdm
91. Xaa Val Xab Pro Xdn
92. Xaa Val Xab Pro Xdo
93. Xaa Val Xab Pro Xdp
94. Xaa Val Xab Pro Xdq
95. Xaa Val Xab Pro Pro Xdr
96. Xaa Val Xab Pro Xds
97. Xaa Val Xbc Pro Xcv
98. Xaa Ile Xab Pro Xay
99. Xcv Val Xab Pro Xay
100. Xaa Val Xbc Pro Xal
101. Xaa Val Xdl Pro Xal
102. Xaa Xdr Xab Pro Xal
103. Xaa Ile Xab Pro Xal
104. Xdd Val Xab Pro Xal
105. Xde Val Xab Pro Xal
106. Xcx Val Xab Pro Xcy
107. Xcw Val Xab Pro Xal
108. Xcx Val Xab Pro Xal
109. Xcw Val Xab Pro Xav
110. Xcx Val Xab Pro Xav
111. Xcw Val Xab Pro Xaw
102. Xcx Val Xab Pro Xaw
103. Xab Val Xab Pro Xay
114. Xab Val Xab Pro Xcv
115. Xab Val Xab Pro Xal
116. Xao Val Xab Pro Xam
117. Xab Val Xab Pro Xan
118. Xab Val Xab Pro Xao
119. Xab Val Xab Pro Xav
120. Xab Val Xab Pro Xaw
121. Xab Val Xab Pro Xat
122. Xab Val Xab Pro Xau
123. Xab Val Xab Pro Xbf
124. Xab Val Xab Pro Xbm
125. Xab Val Xab Pro Xbn
126. Xab Val Xab Pro Xbo
127. Xab Val Xab Pro Xch
128. Xaa Val Xab Pro Xdt
129. Xaa Val Xab Pro Xdu
130. Xaa Val Xab Pro Xdv
131. Xaa Val Xab Pro Xdw
132. Xaa Val Xab Pro Xdx
133. Xaa Val Xab Pro Xdy
134. Xaa Val Xab Pro Xdz
135. Xaa Val Xab Pro Xea
136. Xaa Val Xab Pro Xeb
137. Xaa Val Xab Pro Xec
138. Xaa Val Xab Pro Xed
139. Xaa Val Xab Pro Xef
140. Xaa Val Xab Pro Xeg
141. Xaa Val Xab Pro Xeh
142. Xaa Val Xab Pro Xei
143. Xaa Val Xab Pro Xek
144. Xaa Val Xab Pro Xel
145. Xaa Val Xab Pro Xem
146. Xaa Val Xab Pro Xen
147. Xaa Val Xab Pro Xeo
148. Xaa Val Xab Pro Xep
149. Xaa Val Xab Pro Xeq
151. Xaa Val Xab Pro Xcg

Examples for the MS-characterization of the synthesized novel compounds are given in the following table.

| EXAMPLE [No.] | Fast atom bombardment MS analysis [Mol.-Weight (measured)] |
|---|---|
| 3. | 565 |
| 4. | 579 |
| 5. | 593 |
| 6. | 607 |
| 7. | 621 |
| 8. | 635 |
| 11. | 607 |
| 12. | 607 |
| 13. | 621 |
| 14. | 649 |
| 15. | 635 |
| 16. | 635 |
| 17. | 635 |
| 18. | 635 |
| 19. | 621 |
| 20. | 621 |
| 21. | 635 |
| 22. | 635 |
| 25. | 633 |
| 26. | 647 |
| 27. | 661 |
| 31. | 623 |
| 32. | 671 |
| 33. | 667 |
| 34. | 631 |
| 35. | 655 |
| 36. | 655 |
| 37. | 669 |
| 38. | 621 |
| 39. | 635 |
| 41. | 649 |
| 42. | 621 |
| 43. | 633 |
| 44. | 667 |
| 45. | 607 |
| 46. | 647 |
| 47. | 668 |
| 48. | 655 |
| 49. | 669 |
| 50. | 685 |
| 51. | 629 |
| 52. | 625 |
| 53. | 721 |
| 55. | 579 |
| 58. | 623 |
| 61. | 597 |
| 62. | 621 |
| 63. | 609 |
| 64. | 625 |
| 65. | 635 |
| 66. | 591 |
| 67. | 715 |
| 68. | 685 |
| 69. | 685 |
| 70. | 591 |
| 71. | 607 |
| 72. | 621 |
| 74. | 706 |
| 75. | 579 |
| 76. | 579 |
| 77. | 579 |
| 78. | 607 |
| 79. | 607 |
| 80. | 607 |
| 81. | 607 |
| 82. | 637 |
| 83. | 692 |
| 84. | 706 |
| 85. | 706 |
| 86. | 706 |
| 87. | 607 |
| 90. | 635 |
| 92. | 659 |

-continued
| EXAMPLE [No.] | Fast atom bombardment MS analysis [Mol.-Weight (measured)] |
|---|---|
| 93. | 617 |
| 94. | 636 |
| 95. | 678 |
| 128. | 671 |
| 131. | 625 |
| 139. | 625 |
| 151. | 637 |
TABLE I
Sequence Identification of Compounds Prepared According to Examples 1 and 2
| Compound Number(s) |
|---|
| 1-56, 58-72, 75, 77, 79, 80, 82, 87-94, 96, 97, 99-101, 104-151 |
| 73, 74, 83-86, 95, |
| 57, 76, 81, 102 |
| 78, 98, 103 |
The symbols Xaa in the summa-ay have the following meanings:
| Xaa: | N,N-Dimethylvaline |
| Xab: | N-Methylvaline |
Xac:
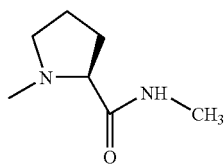
Xad:
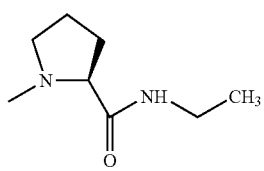
Xae:
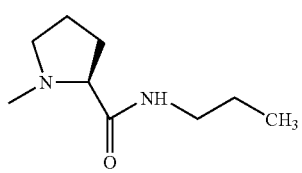
Xaf:
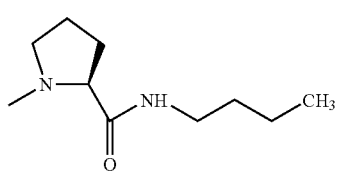
Xag:
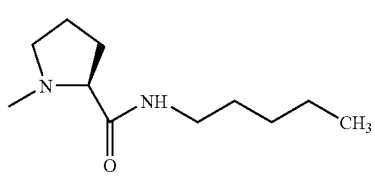
Xah:
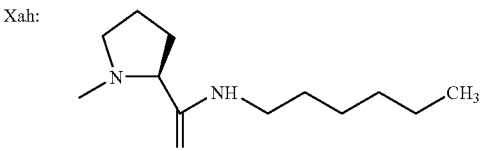
Xai:
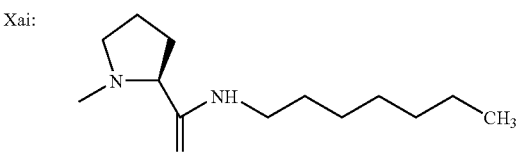
Xak:
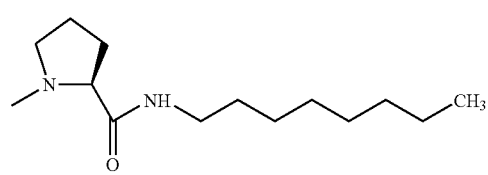
Xal:
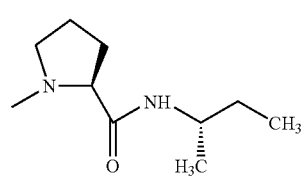
Xam:
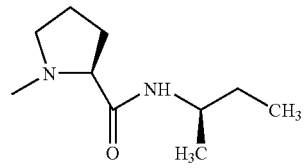
Xan:
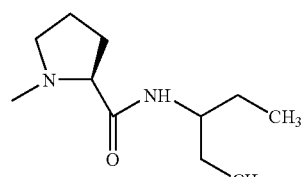
Xao:
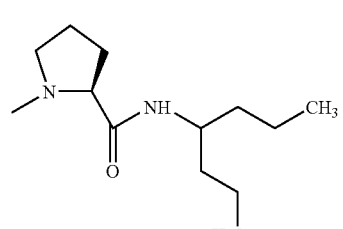
Xap:
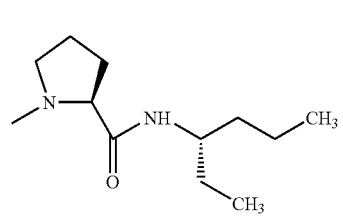

-continued
Xaq: 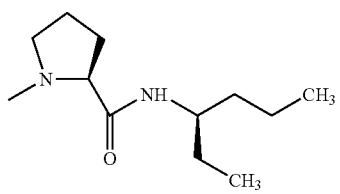
Xar: 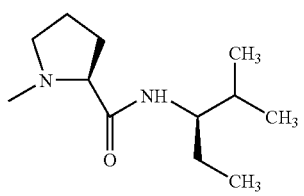
Xas: 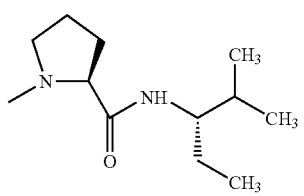
Xat: 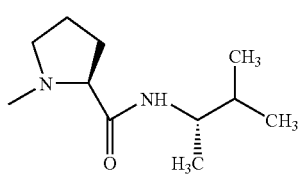
Xau: 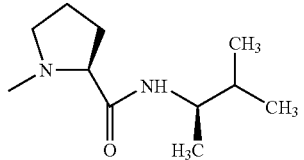
Xav: 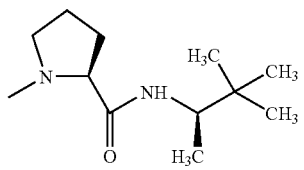
Xaw: 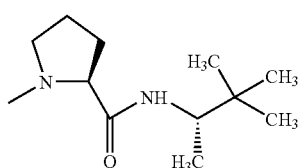
Xax: 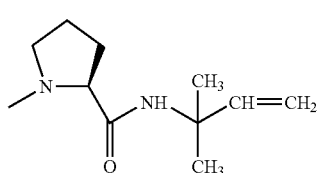
-continued
Xay: 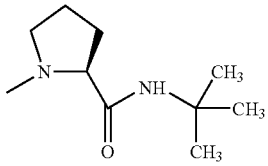
Xaz: 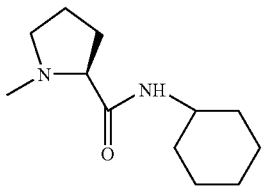
Xba: 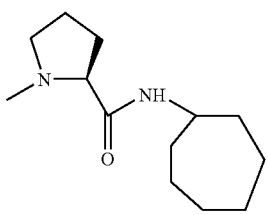
Xbb: 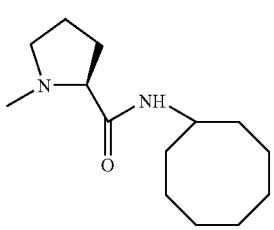
Xbc: N-Methyl-isoleucine
Xbd: 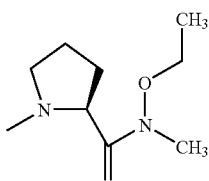
Xbe: 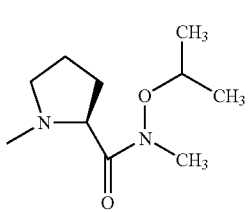
Xbf: 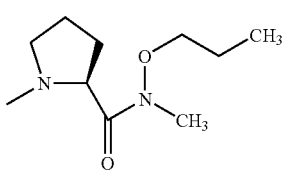
Xbg: 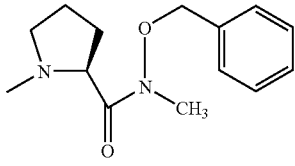

-continued
Xbh: 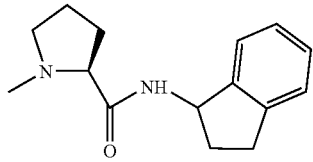
Xbi: 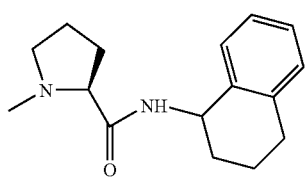
Xbk: 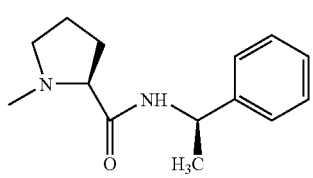
Xbl: 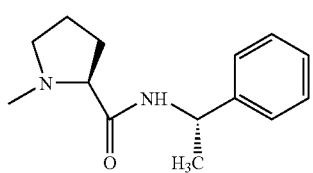
Xbm: 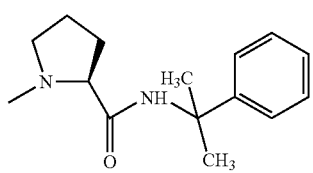
Xbn: 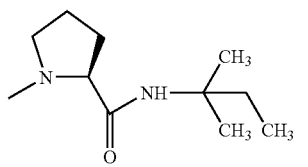
Xbo: 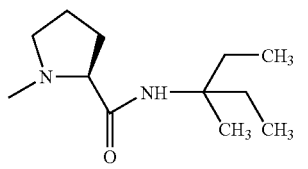
Xbp: 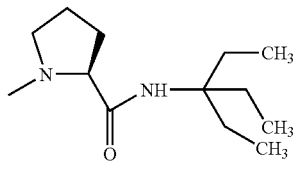
-continued
Xbq: 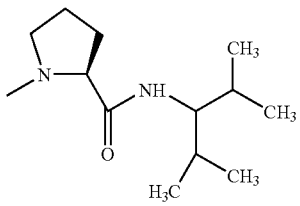
Xbr: 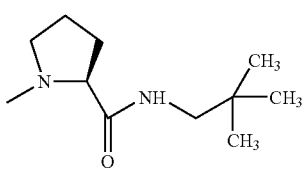
Xbs: 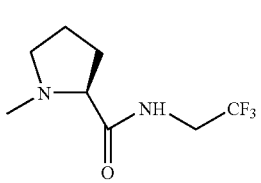
Xbt: 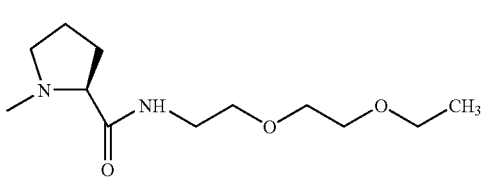
Xbu: 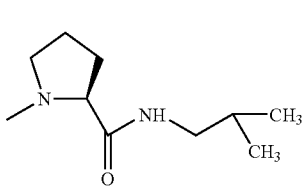
Xbv: 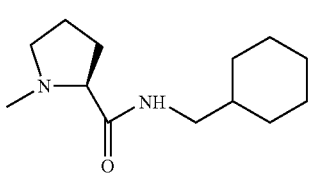
Xbw: 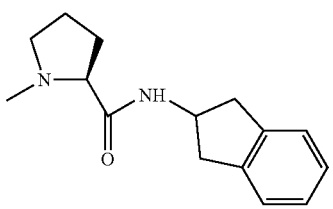
Xbx: 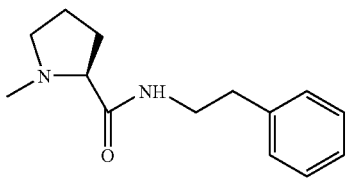

-continued
Xby: 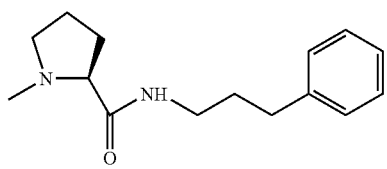
Xbz: 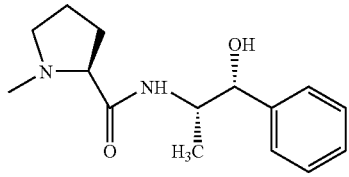
Xca: 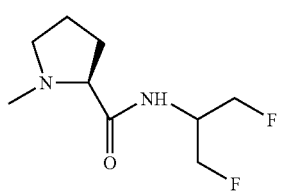
Xcb: 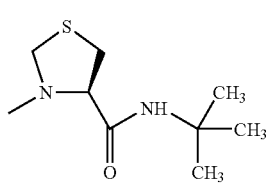
Xcc: Proline adamantyl(l)amide
Xcd: 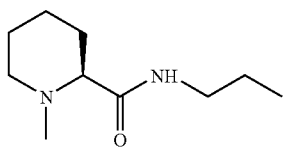
Xce: 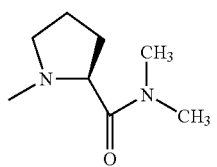
Xcf: 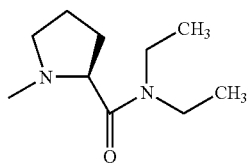
Xcg: 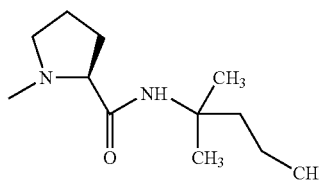
-continued
Xch: 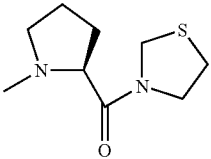
Xci: 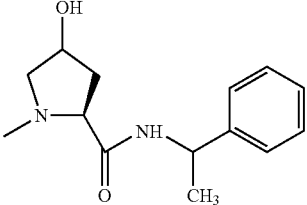
Xck: 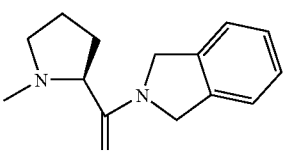
Xcl: 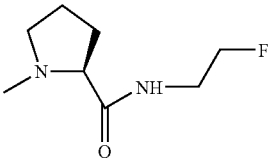
Xcm: 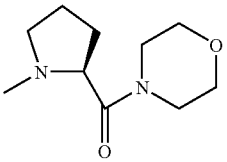
Xcn: 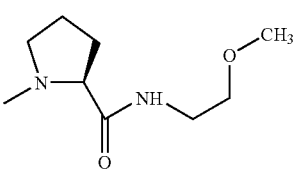
Xco: 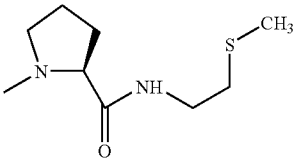
Xcp: 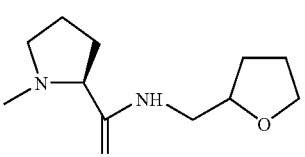
Xcq: 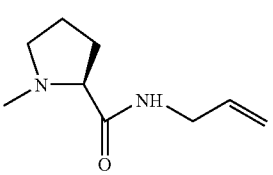

Xcr: 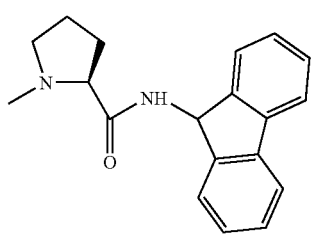
Xcs: 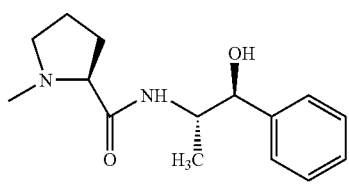
Xct: 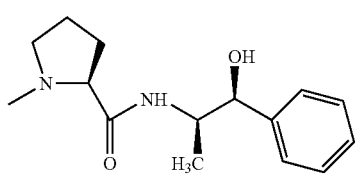
Xcu: 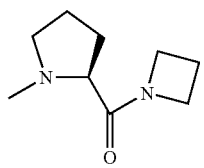
Xcv: 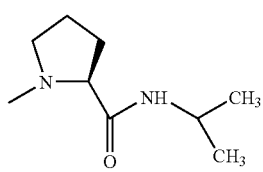
Xcw: N-Methyl-N-ethyl-valine
Xcx: N,N-Diethylvaline
Xcy: 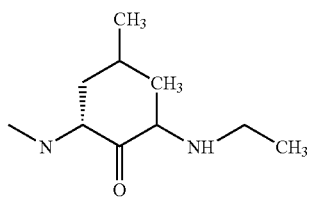
Xcz: 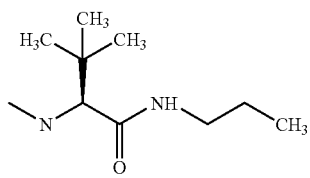
Xda: N-Methyl-2-aminobutyroyl
Xdb: 2-aminobutyroyl
Xdc: N,N-Dimethyl-2-aminobutyroyl
Xdd: N,N-Dimethyl-2-tert.butylglycine
Xde: N,N-Dimethyl-isoleucine
Xdf: 2-tert.butylglycine
Xdg: 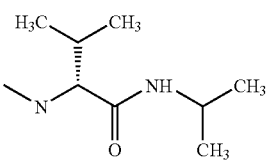
Xdh: 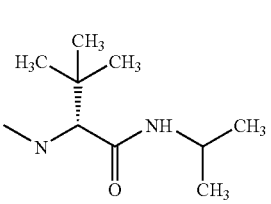
Xdi: 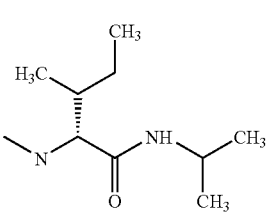
Xdk: 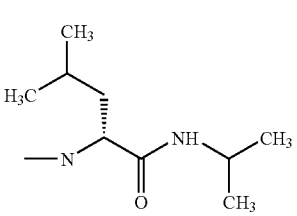
Xdl: N-Methyl-2-tert-butylglycine
Xdm: 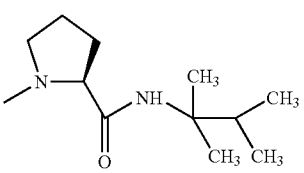
Xdn: 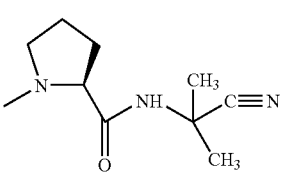
Xdo: 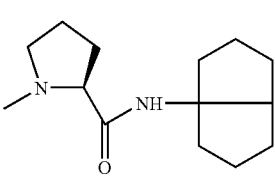
Xdp: 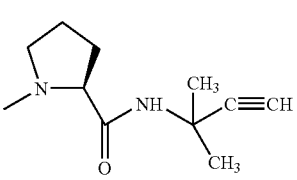

Xdq: 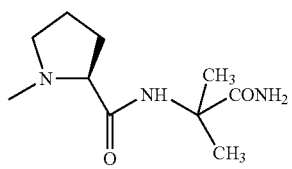
Xdr: 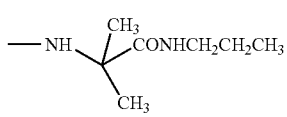
Xds: 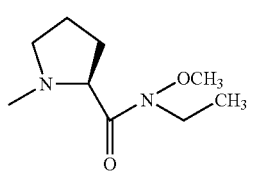
Xdt: 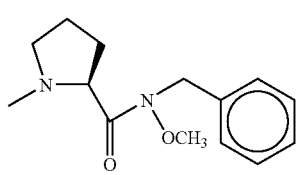
Xdu: 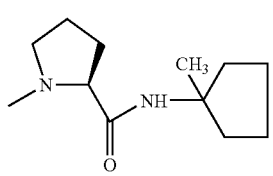
Xdv: 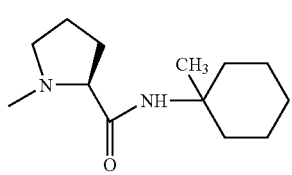
Xdw: 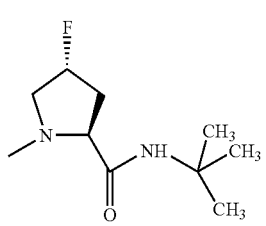
Xdx: 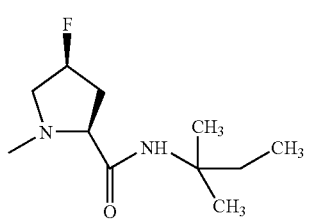
Xdy: 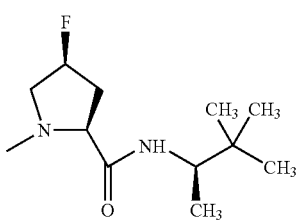
Xdz: 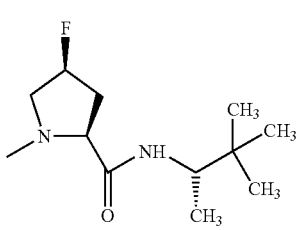
Xea: 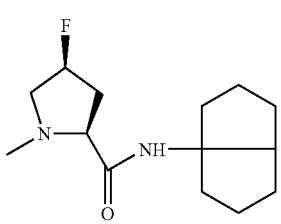
Xeb: 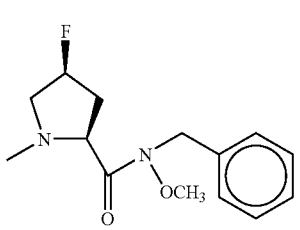
Xec: 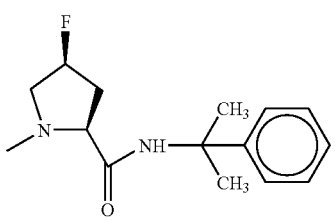
Xed: 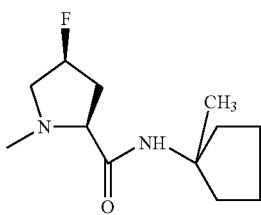
Xee: 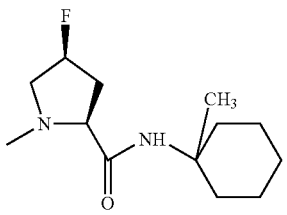

-continued

Xef: 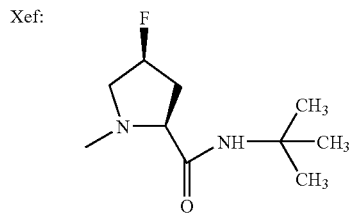

Xeg: 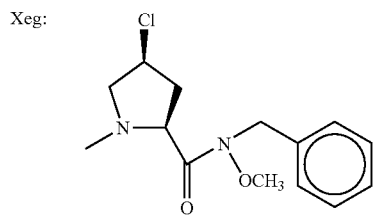

Xeh: 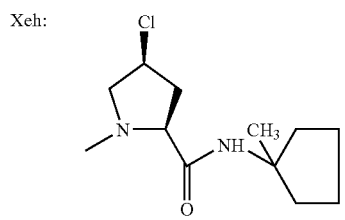

Xei: 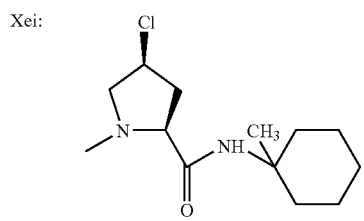

Xek: 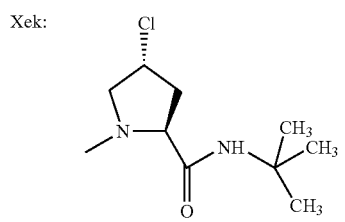

Xel: 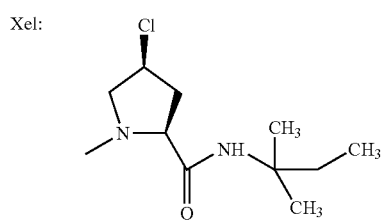

Xem: 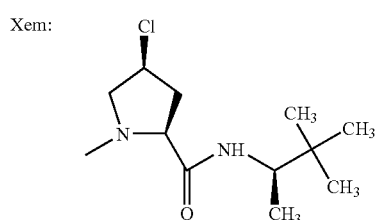

-continued

Xen: 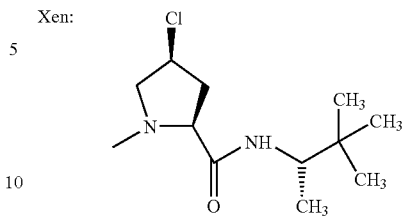

Xeo: 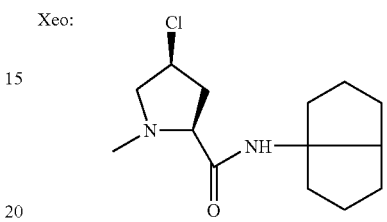

Xep: 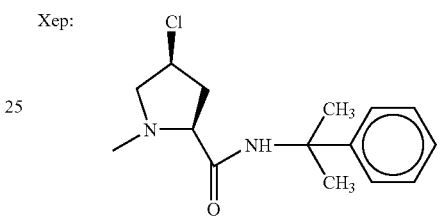

Xeq: 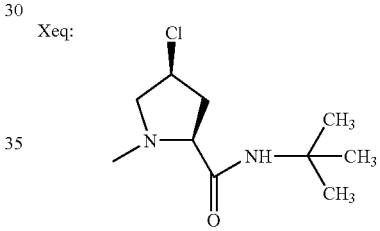

Compounds of this invention may be assayed for anti-cancer activity by conventional methods, including for example, the methods described below.

A. In vitro Methodology

Cytotoxicity was measured using a standard methodology for adherent cell lines such as the microculture tetrazolium assay (MTT). Details of this assay have been published (Alley, M C et al, Cancer Research 48:589-601, 1988). Exponentially growing cultures of tumor cells such as the HT-29 colon carcinoma or LX-1 lung tumor are used to make microtiter plate cultures. Cells are seeded at 3000 cells per well in 96-well plates (in 150 µl or media), and grown overnight at 37° C. Test compounds are added, in 10-fold dilutions varying from $10^{-4}$ M to $10^{-10}$ M. Cells are then incubated for 72 hours. To determine the number of viable cells in each well, the MTT dye is added (50 µl or 3 mg/ml solution of 3-(4,5-dimethylthiazol-2-yl)-2,5-diphenyltetrazolium bromide in saline). This mixture is incubated at 37° C. for 5 hours, and then 50 µl of 25% SDS, pH2 is added to each well. After an overnight incubation, the absorbance of each well at 550 nm is read using an ELISA reader. The values for the mean ±SD of data from replicated wells are calculated, using the formula % T/C (% viable cells treated/control).

$$\frac{OD \text{ of treated cells}}{OD \text{ of control cells}} \times 100 + \% \ T/C$$

The concentration of test compound which gives a T/C of 50% growth inhibition was designated as the $IC_{50}$ value.

B. In vivo Methodology

Compounds of this invention were further tested in preclinical assay for in vivo activity which is indicative of clinical utility. Such assays were conducted with nude mice into which tumor tissue, preferably of human origin, had been transplanted (xenografted), as is well known in this field. Test compounds were evaluated for their anti-tumor efficacy following administration to the xenograft-bearing mice.

More specifically, human breast tumors (MX-1) which had been grown in athymic nude mice were transplanted into new recipient mice, using tumor fragments which were about 50 mg in size. The day of transplantation was designated as day 0. Six to ten days later, mice were treated with the test compounds given as an intravenous injection or orally, in groups of 5-10 mice at each dose. Compounds were given every other day, for 3 weeks, at doses from 1-200 mg/kg body weight.

Tumor diameters and body weights were measured twice weekly. Tumor volumes were calculated using the diameters measured with Vernier calipers, and the formula (Length×width$^2$)/2=mm$^3$ of tumor volume Mean tumor volumes are calculated for each treatment group, and T/C values determined for each group relative to the untreated control tumors.

The new compounds possess good tumor inhibiting properties.

The invention claimed is:

1. A synthesized peptide of the formula I:

$Me_2$Val-Val-MeVal-Pro-Pro-NHC$(CH_3)_3$ (SEQ ID NO: 1)  (I)

and the salt thereof with physiologically tolerated acids.

2. The peptide of claim 1 wherein the peptide of formula I is in the hydrochloride form.

* * * * *

```
                        SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
          (A) LENGTH: 5 amino acids
          (B) TYPE: amino acid
          (D) TOPOLOGY: linear (ii) MOLECULE TYPE: peptide (vi) ORIGINAL SOURCE:
          (A) ORGANISM: /Artificial sequence (ix) FEATURE:
          (D) OTHER INFORMATION: /Artificial sequence (xi) SEQUENCE DESCRIPTION: SEQ ID NO: 1:

Xaa Val Xaa Pro Xaa
 1               5

(2) INFORMATION FOR SEQ ID NO: 2:

(i) SEQUENCE CHARACTERISTICS:
          (A) LENGTH: 6 amino acids
          (B) TYPE: amino acid
          (D) TOPOLOGY: linear (ii) MOLECULE TYPE: peptide (vi) ORIGINAL SOURCE:
          (A) ORGANISM: /Artificial sequence (ix) FEATURE:
          (D) OTHER INFORMATION:  /Artificial sequence (xi) SEQUENCE DESCRIPTION: SEQ ID NO: 2:

Xaa Val Xaa Pro Pro Xaa
 1               5

(2) INFORMATION FOR SEQ ID NO: 3:

(i) SEQUENCE CHARACTERISTICS:
          (A) LENGTH: 5 amino acids
```

```
            (B) TYPE: amino acid
            (D) TOPOLOGY: linear (ii) MOLECULE TYPE: peptide (vi) ORIGINAL SOURCE:
            (A) ORGANISM: /Artificial sequence (ix) FEATURE:
            (D) OTHER INFORMATION: /Artificial sequence (xi) SEQUENCE DESCRIPTION: SEQ ID NO: 3:

Xaa Xaa Xaa Pro Xaa
 1               5

(2) INFORMATION FOR SEQ ID NO: 4:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (vi) ORIGINAL SOURCE:
            (A) ORGANISM: /Artificial sequence (ix) FEATURE:
            (D) OTHER INFORMATION: /Artificial sequence (xi) SEQUENCE DESCRIPTION: SEQ ID NO: 4:

Xaa Ile Xaa Pro Xaa
 1               5
```